(12) United States Patent
Melrose

(10) Patent No.: US 9,119,394 B2
(45) Date of Patent: Sep. 1, 2015

(54) ANTI-MICROBIAL POLYMERS AND THEIR COMPOSITIONS

(75) Inventor: Graham J. H. Melrose, Mount Claremount (AU)

(73) Assignee: RECCE PTY LTD., Mount Claremont, Western Australia (AU)

( * ) Notice: Subject to any disclaimer, the term of this patent is extended or adjusted under 35 U.S.C. 154(b) by 236 days.

(21) Appl. No.: 12/774,057

(22) Filed: May 5, 2010

(65) Prior Publication Data

US 2010/0266527 A1 Oct. 21, 2010

Related U.S. Application Data

(63) Continuation-in-part of application No. PCT/AU2008/001140, filed on Aug. 6, 2008.

(30) Foreign Application Priority Data

| Nov. 7, 2007 | (AU) | ................................ | 2007906124 |
| Dec. 14, 2007 | (AU) | ................................ | 2007906829 |
| Jul. 11, 2008 | (AU) | ................................ | 2008903576 |

(51) Int. Cl.

| A61K 31/78 | (2006.01) |
| A61K 31/765 | (2006.01) |
| A61P 31/00 | (2006.01) |
| A01N 35/02 | (2006.01) |
| A01N 37/36 | (2006.01) |
| A01N 43/16 | (2006.01) |
| C08G 2/24 | (2006.01) |

(52) U.S. Cl.
CPC ................ *A01N 35/02* (2013.01); *A01N 37/36* (2013.01); *A01N 43/16* (2013.01); *A61K 31/78* (2013.01); *C08G 2/24* (2013.01)

(58) Field of Classification Search
USPC ........................................................ 528/271
See application file for complete search history.

(56) References Cited

U.S. PATENT DOCUMENTS

| 6,060,571 | A * | 5/2000 | Werle et al. .................... 526/315 |
| 6,410,040 | B1 * | 6/2002 | Melrose et al. ................ 424/404 |
| 6,723,336 | B1 * | 4/2004 | Melrose ........................ 424/438 |
| 6,803,356 | B1 * | 10/2004 | Melrose et al. ................ 510/475 |
| 2004/0170599 | A1 * | 9/2004 | Melrose ..................... 424/78.31 |
| 2007/0083031 | A1 * | 4/2007 | Tilbrook ....................... 528/230 |

FOREIGN PATENT DOCUMENTS

| WO | WO 96/38186 | 12/1996 |
| WO | WO 00/03723 | 1/2000 |
| WO | WO 01/60874 | 8/2001 |
| WO | WO 2005/044874 | 5/2005 |

OTHER PUBLICATIONS

March, Jerry; Advanced Organic Chemistry: Reactions, Mechanisms, and Structure; 1977; McGraw-Hill, Inc.; pp. 810-811.*

* cited by examiner

*Primary Examiner* — Michael B Pallay
(74) *Attorney, Agent, or Firm* — Vedder Price, P.C.; Thomas J. Kowalski; Deborah L. Lu

(57) ABSTRACT

Polymers derived directly from acrolein monomer that are substantially soluble in water and/or aqueous media, together with methods for preparing same and compositions containing such for use as an anti-microbial, anti-cancer, anti-inflammatory and/or anti-coagulant.

5 Claims, No Drawings

ANTI-MICROBIAL POLYMERS AND THEIR COMPOSITIONS

INCORPORATION BY REFERENCE

This application is a continuation-in-part application of international patent application Serial No. PCT/AU2008/001140 filed 6 Aug. 2008, which published as PCT Publication No. WO 2009/059350 on 14 May 2009, which claims benefit of Australian patent application Serial Nos. 2007906124 filed 7 Nov. 2007, 2007906829 filed 14 Dec. 2007 and 2008903576 filed 11 Jul. 2008.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to anti-microbial polymers and their compositions. The polymers are derived from the aqueous, base-catalysed polymerisation of acrolein and/or its acetals with hydroxy-alkanoic acids—optionally in the presence of ascorbic acid and/or anti-oxidant and/or alkanol. The present invention is in part directed to the manufacture of these compounds, and in vitro or in vivo uses of the compositions derived therefrom, especially as anti-microbial agents within the gastro-intestinal tracts of humans or animals.

BACKGROUND OF THE INVENTION

A "pure" polymer is inherently a mixture of different molecules. These molecules have different molecular weights, and often, different configurations—depending upon the polymerisation conditions by which the polymer was formed from its monomer(s). As a result, the mode of polymerisation of the monomer determines the chemical structure and hence, all properties of the polymer. It is groundless and most often wrong to assume that all polymers from the one monomer are either the same or react in the same manner. In particular, acrolein (2-propene-1-al) has alternative reaction-sites and every "polyacrolein" is not the same.

The polymerisation of acrolein was first reported[1] in 1843—providing a solid, insoluble in all common solvents, and of no significant use.

Much later in 1987, Melrose et al[2] first described the manufacture, compositions and uses of a range of polymers of acrolein as anti-microbial agents; by demonstrating a structural analogy between the polymers and the chemical sterilant glutaraldehyde (pentane-1,5-dial), the carbonyls were assigned as the anti-microbial sites in the polymers. Since water is the growth-domain of nearly all micro-organisms, water-solubility or at least an ability to disperse is essential for anti-microbial activity against these micro-organisms; therefore, usually, the polymers also contained hydrophilic co-monomers, so as to make the polymers more water-soluble. But still, anti-microbial activity of the polymers remained low, due to their high content of co-monomer which only contributed hydrophilicity.

In an attempt to circumvent this limiting insolubility in water—subsequent references[3-7] always requires firstly, the anionic homo-polymerisation of acrolein monomer only, to yield an insoluble polyacrolein. Therefore, this was followed by secondly, filtration of the resulting water-insoluble polymer—then thirdly, prolonged autoxidation of the polymer by heating in air or oxygen over several days, to yield the acrolein-polymer, poly (2-propenal, 2-propenoic acid) having a content of 0.1 to 5 moles of (hydrophilic) carboxyl/Kg of polymer, so as to achieve water-solubility, albeit only[4] at pHs above 5.5. Fourthly, the auto-oxidised polymer may be treated with polyethylene glycol (PEG) over a range including both weakly basic then weakly acidic conditions, to yield an acrolein-polymer having increased hydrophilicity, and acetal groups derived from reaction with the polyethylene glycol. However, this sequential synthesis is substantially limited, in that its autoxidation-step is so protracted—and tenuous, due to the well-known propensity of acrolein-polymers to revert to insoluble gums during filtration, and especially upon heating—a property[8] which had inhibited their use for over one hundred years. As a direct consequence of these disadvantages, this process can not be repeated, successfully, on a regular basis.

Within the gastro-intestinal tract of humans, the bacterium *Helicobacter pylori*[10] may be harboured in tooth-plaque; also surrounded by protective natural polymers, it is found in the stomach of about 50% of persons world-wide. In humans, it is unequivocally associated with stomach and duodenal ulcers and cancer; noteworthy, the bacterium thrives within the acidic pHs of the stomach. Therapy for infected patients necessarily includes a regime of a range of different antibiotics—since it is increasingly being frustrated by strains of *H. pylori* which are resistant to known antibiotics. In animals, but with less certainty, other *Helicobacter* have also been associated with gastro-intestinal disease.

Always, soluble polymers of acrolein have shown an exceptionally wide range of anti-microbial activity—even against antibiotic-resistant germs—and this is explained by the polymers' content of carbonyl groups which react destructively and indiscriminately with ever-present proteins in the outer membranes of all micro-organisms. Particularly, Melrose et al[7] have reported anti-microbial activity of the acrolein-polymer, poly (2-propenal, 2-propenoic acid) against *H. pylori*, in vitro at pH 4 or pH 7—but the polymer's water-solubility and anti-microbial activity is greatly reduced at the lower pHs associated with stomach-contents (that is, below pH 4).

Acrolein can be a source of extreme irritation to humans or animals[3-7, 9]. It is generally recognised that any molecule having molecular weight less than 800, reasonably freely passes through natural membranes (skin or intestines); thus, irritating acrolein-monomer, low molecular weight oligomers of acrolein or its acetals have the propensity to penetrate protective membranes in humans or animals and hence, enter the vascular system, causing irritation.

Specification WO 2005/044874 relates to a method for the manufacture of what are referred to as soluble, microbiologically active and stable acrolein polymers. Importantly, the polymer described is not derived directly from acrolein and is subject to the known problems associated with the initial filtration of a derived acrolein and is consequently limited by the formation of emulsions and gums. These issues have been highlighted[4]. The polymers produced by this method are not significantly anti-microbial and the minimum kill concentrations (MKC's) disclosed in the specification are known to involve a 24 hr exposure time. The method of manufacture described includes a number of limitation in addition to that noted immediately above. These include autoxidation/severe heating conditions at 65° C. and above (which are described as essential), derivation in acidic conditions, a requirement for subsequent treatment of the polymer with base to achieve stability, substantial degradation of the polymer as evidenced by the brown colour thereof, and the polymer derived in this manner is further poly-acetal and contains considerable carboxyl as is apparent from its dissolution in sodium carbonate solution (normally about pH 11) only giving a pH of 8 as the result of neutralisation of carboxyl.

Citation or identification of any document in this application is not an admission that such document is available as prior art to the present invention.

SUMMARY OF THE INVENTION

In this invention, polymerisations to yield a range of novel and useful polymers of acrolein and/or its acetals with hydroxy-alkanoic acids are described, so as to give distinct polymers of different and desired physical, chemical and anti-microbial properties.

It is one (first) objective of this invention, to provide novel, anti-microbial and water-soluble polymers of acrolein by a practical synthetic route—and in particular, in so doing, to avoid the necessity of proceeding through an autoxidation-step of polymer.

Indeed, if tested, every acrolein-polymer which is soluble in aqueous solvents—has demonstrated anti-microbial activity. However, it is a central tenet of this invention that there has always been a challenging compromise to this latent anti-microbial property of all acrolein-polymers: It is solubility. Particularly, lack of solubility compromises the manifestation of the polymers' substantial and broad anti-microbial properties over low pH ranges in water.

It is a second objective of this invention to provide novel polymers from acrolein, such that the polymers are soluble over the low pH ranges found within the stomach of humans, and associated with the growth of especially, *H. pylori*.

It is a third objective of this invention to provide polymers from acrolein which are novel, water-soluble at all pHs and anti-microbial—and also having structures with fewer propensities to migrate across membranes.

In this specification:

(a) Unless specifically designated, always, an "alkanol" describes any compound having one or more hydroxyl groups, including hydroxy-derivatives of alkanes, alkenes, alkynes, aromatics, heterocycles, sugars, natural or synthetic polymers;

(b) Unless specifically designated, always, an "hydroxy-alkanoic acid" or "alkanol containing carboxyl(s) groups" includes hydroxy-carboxylic acid-analogues related to alkanes, alkenes, alkynes, aromatics, heterocycles, sugars, natural or synthetic polymers—and as well as referring to mono-functional compounds in either one or both of these functional groups—may also include such compounds containing more than one hydroxyl group and/or more than one carboxyl group and/or other groups which do not materially interfere with the functionality of either the hydroxyl or carboxyl groups;

(c) Unless specifically designated, always, "acetal" may describe mono-acetal and/or di-acetal;

(d) Unless specifically designated, always, "polymerisation", may describe homo-polymerisation and/or co-polymerisation;

(e) Unless specifically designated, always, "olefinic monomer containing carboxyl group(s)" describes an olefin-monomer capable of polymerisation and containing one or more carboxyl groups in any state of ionisation;

(f) Unless specifically designated, always, "acrolein" may describe and/or may include not only the free acrolein-monomer, but also in the same context, the acrolein-residue within a polymer;

(g) Whilst *H. pylori* is discussed in particular herein, the invention is applicable to other *Helicobacter* or other microorganisms, especially amongst others, bacteria, fungi, yeasts, viruses and/or protozoa;

(h) Whilst the present invention is described with reference to acrolein, it is not to be understood as limited thereto, but rather includes derivatives of acrolein (such as, methacrolein).

Throughout the specification and claims, unless the context requires otherwise, the word "comprise" or variations such as "comprises" or "comprising", will be understood to imply the inclusion of a stated integer or group of integers but not the exclusion of any other integer or group of integers.

It is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DETAILED DESCRIPTION

In accordance with the present invention there are provided polymers derived directly from acrolein monomer that are substantially soluble in water and/or aqueous media.

Preferably, the polymers of the present invention are soluble at a pH of less than about 4.

Still preferably, no intermediate autoxidation step is employed in the preparation of the polymers of the present invention.

Still further preferably, the polymers of the present invention are substantially anti-microbial.

Yet still further preferably, the polymers of the present invention have an average molecular weight of greater than about 1000 Daltons. The polymers may be prepared so as to have fewer propensities to migrate through membranes as the result of having high levels of polarity and/or hydrophilicity due to included carboxyl groups, either within hydroxy-alkanoic acids attached to the polymers as acetal groups, or within monomer-residues in the polymers—and whereby these polymers of average molecular weight greater than 1000 Daltons are substantially inhibited from passing through membranes which are designed to be transmissible to all molecules up to molecular weight 1000 Daltons.

The polymers of the present invention may additionally or further be prepared so as to have fewer propensities to migrate through membranes as the result of having within, structures resulting from the reaction between alkanol (and/or its ion) and proximate carbons to the carbonyl in acrolein-residues within the polymers—and whereby these polymers of average molecular weight greater than 1000 Daltons are substantially inhibited from passing through membranes which are designed to be transmissible to all molecules up to molecular weight 1000 Daltons.

The polymers of the present invention preferably have a carboxyl content of between about 0.1 and 25 moles/Kg of polymer.

In accordance with the present invention there is further provided a composition, being a solution, gel, emulsion or suspension of matter comprising at least in part polymers as defined hereinabove.

In accordance with the present invention there is still further provided an in vitro and/or in vivo anti-microbial composition comprising at least in part polymers as defined hereinabove.

In accordance with the present invention there is yet still further provided a method for the synthesis of polymers defined hereinabove, the polymers having been prepared so as to incorporate acetal-structures resulting from the reaction between acrolein (monomer or residue) and hydroxy-alkanoic acid (and/or its ion), or so as to incorporate within, structures resulting from the reaction between alkanol (and/or its ion) and proximate carbons to the carbonyl in acrolein-residues within the polymers.

The method may further comprise the polymerisation, in basic aqueous solution in the presence of a basic catalyst, of acrolein, and/or acrolein plus alkanol, and/or other organic nucleophile, and/or acetal of acrolein with a hydroxy-alkanoic acid—optionally, in solution with other monomer, and/or ascorbic acid (and/or its ion) and/or other antioxidant and/or other acid.

The basic aqueous medium is preferably aqueous sodium hydroxide at a pH of between 9 to 14, further preferably between pH 10 to 13.

The hydroxy-alkanoic acid is preferably tartaric acid and/or ascorbic acid. The acetal is preferably formed by acid-catalysis, further preferably using dilute sulphuric acid. The alkanol is preferably a polyalkylene glycol. The polyalkylene glycol is preferably polyethylene glycol.

The polyethylene glycol preferably has average molecular weight of 200 to 10,000 Daltons. The ratio of polyethylene glycol:acrolein or acrolein incorporated as its acetal, is preferably greater than 1:1 v/v, preferably greater than 4:1 v/v.

Preferably, the monomer is acrylic acid, further preferably at a ratio of acrylic acid:acrolein or acrolein incorporated as its acetal in the range of 0.05 to 0.10:1 w/w. The organic nucleophile is preferably a carboxylic acid. The ratio of ascorbic acid:acrolein or acrolein incorporated as its acetal is preferably in the range of about 0.01 to 10:1.00 w/w. Still preferably, the ratio of ascorbic acid:acrolein or acrolein incorporated as its acetal is in the range 0.1 to 2.0:1.0 w/w—and preferably 0.6:1.0 w/w.

In accordance with the present invention there is still further provided methods for the treatment of cancer, disorders of coagulation, and/or inflammatory disorders, each method comprising the administration to a subject of a pharmaceutically acceptable amount of a polymer as described hereinabove, or a composition containing such.

In accordance with the present invention there is yet still further provided the use of a polymer as described hereinabove in the preparation of a medicament for the treatment of one or more of cancer, disorders of coagulation, and/or inflammatory disorders or conditions.

It is hypothesized herein, that the ubiquitous, complete insolubility of polymers resulting from prior-art polymerisations of acrolein monomer[3-7]—may be inhibited or prevented (and anti-microbial properties manifested) by either one, or a combination of two or three methods; primarily, it is hypothesized that the totality of the insolubility is only consistent with inter-molecular cross-linking within the polymers:

Method 1: As this cross-linking was taking place at alkaline pHs, it was concluded that the rapidly-forming cross-links could not be acetal, since these form only under acidic conditions[11]; hence, the links causing insolubility would likely be of radical-origin and could be inhibited during or after polymerisation by ascorbic acid, (having the properties of a water-soluble anti-oxidant and as well, an acid).

Thus, this first method, using ascorbic acid and/or its ion (see Example 5(a) hereinafter), in accordance with objectives one and two of this invention has been successfully used— without an autoxidation step—to provide polymers which are novel, anti-microbial and water-soluble at all pHs.

It is important to note that all three of the "polyacroleins" derived from references (see Example 1 hereinafter) and the polymer from the above polymerisation of acrolein in the presence of ascorbic acid (Example 5(a))—are very different: Obviously, the final polymer from either synthesis is derived from a different pre-cursor—the referenced polymer, from a second intermediate-polymer (Example 1)—the polymer of this invention, directly from the monomer (Example 5(a)); furthermore, the prior-art polymer is insoluble below pH 4, has a carbonyl-content of 380% and is strongly coloured, indicating substantial conjugation within the molecule— whereas the polymer of this invention is soluble at all pHs below pH 4, has a carbonyl-content of only 40% and is without significant colour or apparently, conjugation. The first intermediate-polymer is totally insoluble and is demonstrably, a different "polyacrolein". Whereas the "polyacrolein", termed the second intermediate-polymer (and being derived from autoxidation of the first intermediate-polymer) is substantially anti-microbial (only a small amount is required for inhibition of microbial growth)—the polymer from this invention is initially, eight-fold less anti-microbial; treatment of this second intermediate-polymer with base and polyethylene glycol, increased by two-fold the amount of polymer required for inhibition (Example 1)—similar treatment of polyacrolein from the present invention, produced the opposite effect, decreasing forty-fold the amount of polymer required for inhibition (Example 5); further, this second intermediate-polymer is also obviously different from the totally soluble polymer herein, in that it is not soluble below pH 5.5.

Method 2: If, during ionic polymerisation by base organic nucleophile, especially alkanol is included—it is hypothesized that the formation of inter-molecular bonds causing insolubility of polymer can be inhibited by steric hindrance between separate molecules—as the result of the alkanol or its ion bonding by Michael-type reaction[11,4] to active (in the sense of active-propensity to lose attached hydrogen), proximate carbons to the carbonyl groups in the polymers—thus forming bulky side-groups in the separate polymer-molecules which inhibit cross-linking and insolubility.

Thus, this second method, using alkanol (see Examples 6 and 7 hereinafter) in accordance with objectives one and two of this invention has been successfully used—without an autoxidation step—to provide polymers which are novel, anti-microbial and water-soluble at all pHs.

The successful prevention of cross-linking and its resultant insolubility of acrolein-polymers in this way, herein (Examples 6 and 7), was initially unexpected, for the reason that previously, polymerisations between acrolein and alkanol have always yielded insoluble polymers[9]. Further, given the immediacy of the precipitations of polymer in references[4], it is additionally unexpected that the reaction brought about by the alkanol during the polymerisation herein is sufficiently fast, so as to prevent any precipitation or even clouding.

The difference between the polymer derived this way herein (Example 7), and the previous polymer (also treated with alkanol)[5] (Example 1) is apparent: Firstly, the polymer of this invention (the former) has been synthesised directly from acrolein monomer—the previous polymer (the latter) has been synthesised from poly (2-propenal, 2-propenoic acid); secondly, the former, having been prepared entirely under basic conditions can not be of acetal structure[11B]—whereas, the latter prepared under conditions including acid-treatment, has been assigned an acetal structure with the alkanol; thirdly, the former is soluble at pHs below 4—the latter is not; fourthly, the former is colourless—the latter is deep red, indicating considerable un-saturation within the molecule; fifthly, the former has a carbonyl-content of 20%—the latter has 380%; sixthly, the former is many-fold more anti-microbially active, inhibiting mixed microbes at 100 ppm and killing $10^6$ E. coli in 3 minutes—whereas for the latter, the parameters were 500 ppm and 3 hours, respectively.

Additionally, the polymer (Example 6) of the present invention has similar differences to previous polymers (Example 1).

In summary, as well as being many-fold more anti-microbial than the "super-activated" polymer of prior-art[5]—the polymers of the present invention are water-soluble over a broad range of pHs, whilst the previously known polymer is not.

Method 3: If, before the polymerisation, at least a portion of the acrolein was converted to its acetal derivative with a hydroxy-alkanoic acid—it is hypothesized that the formation of the inter-molecular bonds causing insolubility can be inhibited, especially under the basic conditions, as the result of inter-molecular repulsion between the ionized carboxyls within the polymer-molecules of the present invention.

Thus, in accordance with objectives one and two of this invention there is provided a third method—without an autoxidation step—for the preparation of polymers which are novel, anti-microbial and water-soluble at all pHs, derived from the polymerisation of acrolein, its derivatives and/or its acetals with hydroxy-alkanoic acid (see Example 3 hereinafter)—optionally, additionally performed in the presence of ascorbic acid, the method also giving in substantial yield, polymers which are water-soluble at all pHs, and anti-microbial (see Example 4 hereinafter).

Further, the novel, anti-microbial polymers of acrolein provided by all three methods have practical levels of stability under simulated pH and resident-time within the stomach.

By design herein, another important advantage in forming the acetals with hydroxy-alkanoic acid is that it renders the polymers more hydrophilic, causing the polymers to have fewer propensities to migrate across biological membranes in vivo; it is well-known in the art that increased hydrophilicity slows migration.

Thus, in accordance with a third objective of the present invention, there are provided polymers of acrolein which are novel, anti-microbial, soluble at all pHs—and which have a reduced propensity to migrate across biological membranes.

The polymers derived from the co-polymerisation of an acetal, according to the present invention have a carboxyl-content of about 0.1 to 15 moles/Kg of polymer—preferably about 5 to 10 moles carboxyl/Kg of polymer. That is, usually, the novel polymers have higher carboxyl contents than those of previously known polymers—and a reduced propensity to migrate across biological membranes.

During dialyses, these polymers were inhibited from travel through membrane which is designed to be permeable to all molecules up to 10,000 Daltons.

Herein, for estimations of anti-microbial activity, an assay of inhibition of growth of micro-organisms in milk was chosen, as milk contains a wide range of different micro-organisms, and contains proteinaceous materials which usually, readily bind-with and de-activate acrolein-polymers. The Examples provided hereinafter show that this invention provides substantially anti-microbial polymers—in these demanding conditions. Also, the polymers were estimated against diarrhea-producing bacteria, Escherichia coli.

The polymers of Examples 4 and 7 hereinafter are two preferred polymers of the present invention—both are prepared without an autoxidation step—are soluble at all pHs—and have structures designed to give minimal migration across membranes relative to that of previous acrolein polymers. Additionally, a summary of results from these estimations for these polymers, and the best previously known polymer (Example 1) shows that there is also provided herein, polymers which are considerably more anti-microbial than any previously-known acrolein-polymers:

TABLE 1

Comparison of Polymeric Anti-microbials (See "Examples" section for details of methods)

| Example | Minimum amount for total kill (ppm) | Time to kill E. coli (mins.) |
|---------|-------------------------------------|------------------------------|
| 4       | 250                                 | 180                          |
| 7       | 50                                  | 3                            |
| 1       | 500                                 | 180                          |

BEST MODE(S) FOR CARRYING OUT THE INVENTION

In chronological order, the method of the present invention comprises the following, outline steps:

1. Optionally, partial conversion, using acid-catalyst, of acrolein monomer to its acetal derivative with an hydroxy-alkanoic acid;

2. Polymerisation in basic aqueous solution and providing a basic catalyst, of acrolein, and/or acrolein plus alkanol and/or other organic nucleophile(s) (and/or its ion), and/or the product from Step 1 above—optionally, in solution with other monomer(s), and/or ascorbic acid (and/or its ion) and/or other antioxidant and/or other acid; and 3. Adjustment of the resulting solution to pH 7 with acid.

Additionally, at the commencement of Step 3 (before adjustment to pH 7), it will be apparent that all the preparations of this invention are amenable to dialysis against water; especially, this totally removes any low molecular weight fractions which may penetrate membranes, in vivo. However, when applying this technique to the polymer (see Example 4 hereinafter), some loss of anti-microbial activity was observed; alternatively, this can be prevented by dialysis against sodium tartrate solution, adjusted to pH 6. A decrease in carbonyl-content accompanies this alternative and the recovery of anti-microbial activity—and suggests that this acetal-polymer has a different site which causes the anti-microbial activity, other than carbonyl.

The combination of methods (of Examples 4 and 7 hereinafter) within Example 8, discussed hereinafter, represents an additional, preferred methodology of the present invention, and yields a polymer of substantial anti-microbial activity. However, an analogous combination of the methods of Examples 4 and 6 yields a polymer of only insignificant anti-microbial activity (see Example 9 hereinafter). The common element of Examples 8 and 9 is that the carbonyls of polymers from both are hindered by acetal-formation (by inclusion of the common method of acetal-formation from Example 4); the reason for their difference is apparent when it is concluded that the site of anti-microbial activity in the polymer of Example 7 is at its remaining and active carbon atoms with which the PEG reacts—whereas in the polymer of Example 6, all active carbons are reacted with PEG, and the carbonyl groups remain exclusively as the sole site of anti-microbial activity. (Following alternative dialysis-conditions of polymer derived in Example 4—the resultant-polymer which is the more active anti-microbial, has the more lower carbonyl-content; this also indicates an alternative site of activity to the carbonyl groups.) Thus, it is apparent that the method of the present invention has the additional advantage of providing polymers having two different anti-microbial sites—for example, from Examples 4 or 7—or from Example 6, respectively. Particularly, this presents an alternative defense against germs evolving anti-microbial resistance. In Step 1, usually a stoichiometric excess of acrolein over hydroxy-alkanoic acid is used, so that in Step 2, co-polymerisation occurs between the acetal of acrolein and the remaining, excess acrolein.

In Step 1, the hydroxy-alkanoic acid is, for example, tartaric acid, lactic acid, glyceric acid, glycolic acid, citric acid or 2-hydroxy-butanoic acid—or other hydroxy-carboxylic acid conceptually derived from the selective oxidation of a diol, an alkan-diol, a polyol, a poly(oxyalkene), a sugar or other molecule containing multiple hydroxyls, such as ethane-1,2-diol, glycerol or polyethylene glycol. A thiol-analog of a hydroxy-alkanoic acid, for example, glutathione, may also be used.

In Step 1, amongst other evidence herein, acetal-formation is confirmed by contrasting the properties of polymers without acetal (Examples 1 and 5(a)) with polymers containing acetal (Examples 3 and 4, respectively).

As they form cyclic acetals with acrolein—which are more favoured (than linear acetals) in their equilibrium-forming reaction[13]—preferred hydroxy-alkanoic acids are tartaric acid or ascorbic acid, especially the former. Within practical limits, in polymers, the acetal of tartaric acid was stable at pH 2 at 37° C. for 4 hours—conditions associated with the resident period of contents in the stomach.

In Step 2, the preferred base is aqueous sodium hydroxide solution—having a pH between 10 and 13.

In Step 2, the preferred organic nucleophile is an alkanol, although a carboxylic acid may be used; a more preferred alkanol is a polyalkylene glycol, especially polyethylene glycol; the preferred molecular weight of the polyethylene glycol is in the range 200-2000 Daltons. For a given weight-ratio of acrolein to alkanol, higher molecular weights of the alkanol give more hindrance and, polymers which have fewer propensities to migrate through membranes; conversely, lower molecular weight alkanols may be preferred in order for the acrolein polymers to penetrate natural polymers surrounding target-germs. The preferred ratio of polyethylene glycol:acrolein (or its acetal) is greater than 1:1 w/w—and more preferably, greater than 4:1 w/w.

In Step 2, and in keeping with discussion hereinabove, a relatively low stoichiometric ratio of hydroxyl groups with the polyethylene glycol (brought about by a high molecular weight and/or a low concentration of the polyethylene glycol) will leave un-reacted active carbons within the resulting polymer—and favour anti-microbial activity at this site in the polymer; the converse will favour anti-microbial activity at the carbonyl groups within the polymer.

In Step 2, if both tartaric acid and polyethylene glycol are used—MW 2000 of the latter, without heating is much preferred (see Example 8 hereinafter).

In Step 2, ascorbic acid (and/or its ion) is preferred; water-soluble antioxidants other than those known in the art may be used. Ascorbic acid (neutralized with base to prevent the formation of acetal)—when used without augmentation of alkanol as the means of preventing insolubility, should be used at greater than about 0.15 part by weight to every 1.00 part of acrolein or acrolein incorporated as its acetal. Ascorbic acid may contribute as an antioxidant, alkanol or carboxylic acid, to inhibit cross-linking between polymers.

In Step 2, the optional co-monomer (if used) is usually an olefinic monomer containing carboxyl groups—preferably, acrylic acid at about 0.05 to 0.10 part by weight to every 1.00 part of acrolein or acrolein incorporated as its acetal. Also, the co-monomer may contain more than one carboxyl group e.g. maleic acid. The usual purpose in the inclusion of monomer is to provide either repulsion between the molecules (or their ions) during polymerisation, and/or hydrophilicity in the product-polymer.

Polymers of this invention have been provided either as their aqueous solutions (see Examples 2, 5, 8)—or after dialysis, isolated as the dry liquid-polymers (see Examples 4, 6, 7).

The polymers of this invention have physical and anti-microbial stability which makes them practical for their intended uses—and in particular, under the conditions (pH 2/37° C./4 hours) which simulate residence-time in the stomach.

Being free of the protracted autoxidation step—in contrast to previously-known polymers, there is now provided, syntheses of water-soluble and substantially anti-microbial polymers, amenable to the greatly improved economies of continuous-flow manufacture (over the batch-wise manufacture required of the previously-known polymers).

It will be apparent that the examples herein contain laboratory methods; industrially, they will be varied considerably, in ways which are readily apparent to those skilled in the art—and which remain within the spirit and scope of the present invention.

Throughout the description of the present invention, in all methods, the solvent is either aqueous or entirely water. However, the preparations are amenable to heterogeneous techniques—including emulsion, dispersion or suspension techniques.

It is also apparent that the reactions described herein, with free acrolein monomer and/or its derivatives, especially with hydroxy-alkanoic acids—are amenable to the same reactions with fixed acrolein-residues within polymers.

It will be apparent to those skilled in the art that the polymers of this invention may be formulated in controlled-release compositions and/or with other materials as solids, solutions, emulsions, suspensions or gels, into compositions suitable for use in human or animal health care, especially within the gastro-intestinal tract.

The invention will now be further described by way of the following non-limiting examples.

EXAMPLE 1

Previous References[5]

Preparation of Poly (2-Propenal, 2-Propenoic Acid)

With continued stirring at room-temperature, in chronological order:

1. Freshly distilled and inhibitor-free acrolein (15 g) was added to water (180 g); and
2. The pH was adjusted to 10.5 by addition of aqueous sodium hydroxide (ca 5 ml; 0.8% w/w).

After 30 minutes, the insoluble precipitate of the first intermediate-polymer (which had formed within the first minutes) was filtered, then air-dried, firstly at room-temperature for 1 day (dry weight 7.62 g; polymerisation-yield 50%; softening around 80° C.) and then by successive heat-increments to 75° C. over 2 days, followed by heating at 85° C. for 1 day. This resulting second intermediate-polymer dissolved in basic, aqueous solvent to give a deep red solution—but precipitated at pHs below 6; Microbiological Assay showed, minimally, inhibition at 250 ppm of polymer.

A sample of this autoxidized, second intermediate-polymer (5 g) was partly dissolved by stirring and heating at 65° C. in polyethylene glycol (60 g; MW ca 200), and then aqueous sodium hydrogen carbonate (30 g; 1% w/w). The resulting, deep-red solution (pH 8) was heated at 100° C. for 4 hours to yield a solution (final pH 6) of the required (third) acrolein-polymer, namely, poly (2-propenal, 2-propenoic acid).

Microbiological Assay (see all methodologies, below) showed, minimally, inhibition at 500 ppm of polymer, and kill of *E. coli* after 180 minutes; oxidation-products were indicated by a carbonyl assay-result of 380% within the polymer; the polymer precipitated from solution, below pH 4.

The invention is illustrated by the following examples, which should not be regarded as restricting the scope of the invention:

Estimate of Anti-Microbial Activity (a) Microbiological Assay: Inhibition of micro-organisms: Duplicate samples, in serial 50% dilutions, were made-up in aqueous solution (5 ml) and each added to separate stoppered test-tubes containing pasteurised, whole-milk (20 ml) in which sucrose (3 g) had been dissolved. Each resulting sample in the test-tubes was placed in a water-bath at 32-38° C., for 20-24 hours; a "positive" test-tube was prepared and contained water (5 ml) instead of sample-solution (5 ml). The pH of the contents of each was measured before and after these protocols. "Inhibition" was noted when there was greater than 0.5 pH difference between the contents of a test and the "positive"; results are reported as ppm w/w of polymer (assuming polymerisation had proceeded in 100% yield).

Essentially, this assay measures anti-microbial capacity to inhibit a wide range of micro-organisms, and is designed to have relevance to the circumstances of an anti-microbial in the presence of food constituents, at body-temperatures. The accuracy of the assay is considered to be within 1 dilution.

(b) Kill of *Escherichia coli*: In duplicate, samples were dissolved in 1% aqueous sodium bicarbonate so as to give a polymer solution (0.125% w/w of the polymer—assuming 100% polymerisation). A sample of the solution (20 ml) was mixed with 0.1 ml of 10×E6 viable haemolytic *E. coli* (serotype 0149, K88). At time intervals 0, 3, 10, and 180 minutes, an aliquot (in duplicate) was plated on blood agar plates and the counts estimated semi-quantitatively.

Estimate of Carbonyl

This estimate is based upon an established method by Smith[14]. The aqueous sample (1 g) was weighed to an accuracy of 0.01 g—water (9 g) was added, and then the solution of the sample was brought to pH 6.00 by the addition of either 0.01M hydrochloric acid or 0.01M aqueous sodium hydroxide, as appropriate.

A 1% solution of hydroxylamine hydrochloride (50 ml) was brought to pH 6.00 with 0.01M aqueous sodium hydroxide.

The above sample-solution and reagent-solution were mixed and stood at room-temperature for 30 minutes; the reactants were back-titrated with 0.01M aqueous sodium hydroxide (V ml) to pH 6.00.

Then, the w/w % carbonyl content of the original sample (W g)—estimated as acrolein, equals: $(V \times 0.10 \times 5.6)/(W \times f)$ where f is the weight-fraction (expressed as decimal) of polymer within the aqueous sample (assuming a polymerisation yield of 60% which herein, was found in practice, and gave results of carbonyl-content in polymers, comparable and similar to previously-known polymers). Results of duplicate determinations were averaged.

Quantitative Analysis of Polymer Solutions by Dialysis

In duplicate, the aqueous solution of polymer (1.00 g) was dialysed in magnetically-stirred, single-sided micro-dialysis chambers (SIGMA-ALDRICH) against water (1 L) for 4 to 5 hours—using low-binding cellulose acetate membranes (SIGMA-ALDRICH)— as applicable, of upper molecular weight permeability of either 1,000 Daltons or 10,000 Daltons. The dialysates were dried at room-temperature to constant weight, to recover the polymer-fraction.

In Vitro Simulation of Acidic, Resident-Conditions in the Stomach

In duplicate, the aqueous sample (1.00 g) was dissolved in water (9 g) and then made pH2 by the addition of 10% hydrochloric acid; also in duplicate, as the blank, the sample was similarly treated—but substituting the same volume of water for the hydrochloric acid.

All were heated at 37° C./4 hours—then, adjusted to ph 6.00, before analysis of their physical, chemical or microbiological properties.

EXAMPLE 2

With continued stirring at room-temperature, in chronological order:

1. Freshly distilled acrolein (5 g; inhibited with hydroquinone 0.1% w/w) was slowly added to an aqueous solution of ascorbic acid (8.25 g) in water (33 g) containing 1% sulphuric acid (0.25 ml);
2. After 2 hours, the solution was slowly added over 30 minutes to water (100 ml) which was maintained at a pH of ca. 11 by incremental additions of 10% aqueous sodium hydroxide; and
3. After a further 30 minutes, the pH of the clear solution of polymer was adjusted to 7 with 10% hydrochloric acid.

Microbiological Assay showed inhibition minimally at 250 ppm of polymer.

EXAMPLE 3

With continued stirring at room-temperature, in chronological order:

1. Freshly distilled acrolein (5 g; inhibited with hydroquinone 0.1% w/w) was slowly added to an aqueous solution of tartaric acid (7 g) in water (33 g) containing 1% sulphuric acid (0.25 ml);

2. After 2 hours, the solution was slowly added over 30 minutes to water (100 ml) which was maintained at a pH of ca. 11 by incremental additions of 10% aqueous sodium hydroxide; and 3. After a further 30 minutes, the pH was adjusted to 7 with 10% hydrochloric acid, and a minor precipitate of polymer was filtered, washed with a little water, and dried (1.75 g; the polymer did not soften below 125° C.). Most of the polymer remained in solution; its minimum inhibition-quantity was 250 ppm of polymer.

EXAMPLE 4

With continued stirring at room-temperature, in chronological order:

1. Freshly distilled acrolein (5 g; inhibited with hydroquinone 0.1% w/w) was slowly added to an aqueous solution of tartaric acid (7 g) in water (30 ml) containing 1% sulphuric acid (0.25 ml);

2. After 2 hours, the solution was slowly added over 30 minutes to ascorbic acid (5 g) in water (30 ml) which had been brought to, and then maintained at a pH of ca. 11 by incremental additions of 10% aqueous sodium hydroxide; and 3. After a further 30 minutes, the pH was adjusted with 10% hydrochloric acid to give a clear, almost colourless solution of pH 7.5.

When tested down to pH 1, the polymer remained soluble. Microbiological Assay showed inhibition minimally at 250 ppm of polymer—which was unchanged after storage at 7° C./6 months. All *E. coli* were killed after 180 minutes (see method, above). The polymer-solution was dialysed using either a 1,000 Dalton or 10,000 Dalton membrane to isolate the dry liquid-polymer (polymerisation-yield 60%) which inhibited at 500 ppm. Alternatively, the sample inhibited at 500 ppm-1000 ppm after exposure to the simulation of resident-conditions within the stomach at pH 2/37° C./4 hours.

The carbonyl-content within the polymer was 25%—both before and after exposure to simulation of resident-conditions within the stomach at pH 2/37° C./4 hours. The carbonyl-content of the polymer was 55%, and it minimally inhibited at 2000 ppm after dialysis against water, pH 6; the carbonyl-content of the polymer was 5% after dialysis against aqueous sodium tartrate solution (16% w/w; pH 6) and the Microbiological Assay showed inhibition minimally at 500 ppm of polymer.

EXAMPLE 5

With continued stirring, in chronological order:

(a) Freshly distilled acrolein (5 g; inhibited with hydroquinone 0.1% w/w) was slowly added to a pH 11 aqueous solution of ascorbic acid (5 g) in water (19 ml) plus 10% aqueous sodium hydroxide (12 ml); an additional aliquot of the sodium hydroxide solution (1 ml) was added to maintain the pH at 11 during the addition. A small aliquot of this clear, slightly gold solution did not inhibit when tested in the Microbiological Assay until 2000 ppm of polymer.

(b) After 15 minutes, polyethylene glycol 200 (60 ml) was added, and then the clear solution was heated at 50 to 60° C. over 1 hour. The pH was then adjusted to 8 with 10% hydrochloric acid.

A small portion of the clear solution did not precipitate/ cloud down to pH 1; Microbiological Assay showed inhibition minimally at 50 ppm of polymer; the carbonyl-content within the polymer was 40%.

EXAMPLE 6

With continued stirring at room-temperature, in chronological order:

1. Freshly distilled acrolein (5 g; 89 mMole; inhibited with hydroquinone 0.1% w/w) was slowly added to water (20 ml) plus polyethylene glycol (60 ml; 330 mMole; MW 200), rendered pH 12 to 13 by the addition of 10% aqueous sodium hydroxide (2 drops); and 2. After 30 minutes, water (10 ml) was added to the clear, colourless solution, and the pH adjusted to 7 with several drops of 10% hydrochloric acid.

When tested down to pH 1, the polymer remained soluble. Microbiological Assay showed inhibition minimally at 50 ppm of polymer. The recovery of dry liquid-residues after dialyses of polymer-solution, using 1,000 Dalton membranes, gave weights indicating a 1:1 ratio of PEG:acrolein residues.

EXAMPLE 7

With continued stirring at room-temperature, in chronological order:

1. Freshly distilled acrolein (5 g; 89 mMole; inhibited with hydroquinone 0.1% w/w) was slowly added to water (30 ml) plus polyethylene glycol (30 g; 15 mMole; MW 2000), rendered pH 12 to 13 by the addition of 10% aqueous sodium hydroxide (2 drops); and 2. After 60 minutes, the pH of the clear solution was adjusted to 7 with several drops of 10% hydrochloric acid.

When tested down to pH 1, the polymer remained soluble. Microbiological Assay showed inhibition minimally at 100 ppm of polymer, and which was re-produced after storage at 7° C./6 months. All *E. coli* were killed after 3 minutes (see method, above). The inhibition of the polymer was 250 ppm after treatment in the simulation (see above) at pH 2/37° C./4 hours. Dialysis of the polymer-solution, using 10,000 Dalton membrane, then recovery, yielded dry, liquid polymer of weight indicating a 60% polymerisation-yield and approximately 1:6 ratio of PEG:acrolein within the polymer. The dialysis-residue of polymer exhibited microbiological inhibition at 250 ppm; carbonyl-content was determined as 20%.

EXAMPLE 8

With continued stirring at room-temperature, in chronological order:

1. Freshly distilled acrolein (5 g; 89 mMole; inhibited with hydroquinone 0.1% w/w) was slowly added to an aqueous solution of tartaric acid (2.5 g) in water (25 ml) containing 1% sulphuric acid (0.25 ml);

2. After 2 hours, the above solution was slowly added over 15 minutes to ascorbic acid (1 g) plus polyethylene glycol (30 g; 15 mMole; MW 2000) in water (30 ml), pre-rendered to pH 12- and then the reaction maintained at pH 12 to 13 during the addition (by further increments of 10% aqueous sodium hydroxide solution); and 3. After 30 minutes the pH of the clear, pale-golden solution of polymer was adjusted to 7 with 10% hydrochloric acid.

The Microbiological Assay (see above) showed a minimum-inhibition amount at 250 ppm of polymer. The polymer remained soluble in dilute hydrochloric acid of pH 1. Dialysis of the polymer-solution against water, pH 2, gave rise to a solution having a minimum-inhibition amount of 500 ppm of polymer; the recovery of dry polymer gave weights indicating a ratio of 1:11 of PEG:acrolein within the polymer.

EXAMPLE 9

With continued stirring at room-temperature, in chronological order:

1. Freshly distilled acrolein (5 g; 89 mMole; inhibited with hydroquinone 0.1% w/w) was slowly added to an aqueous solution of tartaric acid (2.5 g) in water (25 ml) containing 1% sulphuric acid (0.25 ml);

2. After 2 hours, the above solution was slowly added over 15 minutes to ascorbic acid (1 g) plus polyethylene glycol (30 g; 300 mMole; MW 200) in water (30 ml), pre-rendered to pH 12- and then the reaction maintained at pH 12 to 13 during the addition (by further increments of 10% aqueous sodium hydroxide solution); and 3. After 30 minutes the pH of the clear, golden solution of polymer was adjusted to 7 with 10% hydrochloric acid.

The Microbiological Assay (see above) did not show a minimum-inhibition amount at 2000 ppm of polymer. The polymer remained soluble in dilute hydrochloric acid of pH 1. Recovery of polymer, following dialysis against water, pH 7, gave weights indicating a 1:3 ratio of PEG:acrolein.

It is envisaged that the polymers of the present invention, as a direct result of the properties thereof evident above, will prove effective in the treatment of cancer, disorders of coagulation and inflammation. In turn, it is envisaged that the polymers of the present invention will prove useful and effective when used in anti-cancer, anti-coagulant and anti-inflammatory compositions in a pharmaceutically acceptable amount.

Modifications and variations such as would be apparent to the skilled addressee are considered to fall within its scope.

REFERENCES

1. J. Redtenbacher, *Ann.*, 47, 113 (1843).
2. G. J. H. Melrose, C. M. Kleppe, J. W. Langley, J. M. Stewart and J. Van Dyk, International Patent Publication WO 88/04671.
3. G. J. H. Melrose, International Patent Publication WO 96/38186.
4. G. J. H. Melrose and A. J. Huxham, International Patent Publication WO 00/03723.
5. G. J. H. Melrose, G. Daly and A. J. Huxham, International Patent Publication WO 01/60874 A1.
6. J. A. Staton and G. J. H. Melrose, International Patent Publication WO 02/26211 A1.
7. G. J. H. Melrose, A. J. Huxham, D. M. G. Tilbrook and V. L. Wycoco, International Patent Publication WO 03/061672 A1.
8. R. F. Fischer in C. W. Smith, "Acrolein", John Wiley and Sons, Inc., 1962, Chapter 14, Page 225.
9. P. Werle, H. P. Krimmer, M. Trageser and F. R. Kunz, U.S. Pat. No. 6,060,571.
10. C. Liu and J. M. Crawford in V. Kumar, A. K. Abbas and N. Fausto, "Robbins and Cotran Pathologic Bases of Disease", Elsevier Inc. 7$^{th}$ Edition (International) 2005 Chapter 17, Page 8.
11. M. B. Smith and J. March, "March's Advanced Organic Chemistry, Reactions, Mechanisms, and Structure" John Wiley and Sons, Inc., 5$^{th}$ Edition, 2001. A: Chapter 15, Page 975; B: Chapter 16, Page 1180.
12. G. Odian, "Principles of Polymerisation", John Wiley and Sons, Inc., 2nd Edition 1981, Chapter 5, Page 460.
13. R. C. Morris in Reference 8, Chapter 7, Page 110.
14. E. D. Peters in Reference 8, Chapter 16, Page 256.

The invention is further described by the following numbered paragraphs:

1. Polymers derived directly from acrolein monomer that are substantially soluble in water and/or aqueous media.

2. Polymers according to paragraph 1, wherein the polymers are soluble at a pH of less than about 4.

3. Polymers according to paragraph 1 or 2, wherein no intermediate

4. Polymers according to any one of the preceding paragraphs, wherein the polymers are substantially anti-microbial.

5. Polymers according to any one of the preceding paragraphs, wherein the polymers have an average molecular weight of greater than about 1000 Daltons.

6. Polymers according to any one of the preceding paragraphs, wherein the polymers have a low propensity to migrate through membranes as the result of having high levels of polarity and/or hydrophilicity due to included carboxyl groups, either within hydroxy-alkanoic acids attached to the polymers as acetal groups, or within monomer-residues in the polymers.

7. Polymers according to paragraph 6, wherein the polymers are of average molecular weight greater than 1000 Daltons and are substantially inhibited from passing through membranes which are designed to be transmissible to all molecules up to molecular weight 1000 Daltons.

8. Polymers according to any one of paragraphs 1 to 5, wherein the polymers exhibit a low propensity to migrate through membranes as the result of having within, structures resulting from the reaction between alkanol (and/or its ion) and proximate carbons to the carbonyl in acrolein-residues within the polymers.

9. Polymers according to paragraph 8, wherein the polymers are of average molecular weight greater than 1000 Daltons and are substantially inhibited from passing through membranes which are designed to be transmissible to all molecules up to molecular weight 1000 Daltons.

10. Polymers according to any one of the preceding paragraphs, wherein the polymers have a carboxyl content of between about 0.1 and 25 moles/Kg of polymer.

11. A composition comprising at least in part polymers according to any one of the preceding paragraphs, the composition being a solution, gel, emulsion or suspension of matter.

12. An in vitro and/or in vivo anti-microbial composition comprising at least in part polymers according to any one of the preceding paragraphs.

13. A method for the synthesis of polymers according to any one of paragraphs 1 to 10, wherein the polymers are prepared so as to incorporate acetal-structures resulting from the reaction between acrolein (monomer or residue) and hydroxy-alkanoic acid (and/or its ion), or so as to incorporate within, structures resulting from the reaction between alkanol (and/or its ion) and proximate carbons to the carbonyl in acrolein-residues within the polymers.

14. A method according to paragraph 13, wherein the method further comprises the polymerisation, in basic aqueous solution in the presence of a basic catalyst, of acrolein, and/or acrolein plus alkanol and/or other organic nucleophile, and/or acetal of acrolein with a hydroxy-alkanoic acid—optionally, in solution with other monomer, and/or ascorbic acid (and/or its ion) and/or other antioxidant and/or other acid.

15. A method according to paragraph 14, wherein the basic aqueous solution is preferably aqueous sodium hydroxide at a pH of between about 9 to 14, further preferably between pH 10 to 13.

16. A method according to paragraph 14 or 15, wherein the hydroxy-alkanoic acid is tartaric acid and/or ascorbic acid.

17. A method according to any one of paragraphs 14 to 16, wherein the acetal is formed by acid-catalysis, 18. A method according to paragraph 17, wherein the acid-catalysis uses dilute sulphuric acid.

19. A method according to any one of paragraphs 14 to 18, wherein the alkanol is a polyalkylene glycol.

20. A method according to paragraph 19, wherein the polyalkylene glycol is polyethylene glycol.

21. A method according to paragraph 20, wherein the polyethylene glycol has an average molecular weight of about 200 to 10,000 Daltons.

22. A method according to paragraph 20 or 21, wherein the ratio of polyethylene glycol:acrolein or acrolein incorporated as its acetal, is greater than 1:1 w/w.

23. A method according to paragraph 20, 21 or 22, wherein the ratio of polyethylene glycol:acrolein or acrolein incorporated as its acetal, is greater than 4:1 w/w.

24. A method according to any one of paragraphs 13 to 23, wherein the monomer is acrylic acid.

25. A method according to paragraph 24, wherein the ratio of acrylic acid:acrolein or acrolein incorporated as its acetal is in the range of about 0.05 to 0.10:1 w/w.

26. A method according to any one of paragraphs 14 to 25, wherein the organic nucleophile is a carboxylic acid.

27. A method according to any one of paragraphs 14 to 26, wherein the ratio of ascorbic acid:acrolein or acrolein incorporated as its acetal is in the range of about 0.01 to 10:1.00 w/w.

28. A method according to any one of paragraphs 14 to 27, wherein the ratio of ascorbic acid:acrolein or acrolein incorporated as its acetal is in the range of about 0.1 to 2.0:1.0 w/w.

29. A method according to any one of paragraphs 14 to 28, wherein the ratio of ascorbic acid:acrolein or acrolein incorporated as its acetal is in the range of about 0.6:1.0 w/w.

30. A method for the treatment of cancer comprising the administration to a subject of a pharmaceutically acceptable amount of a polymer according to any one of paragraphs 1 to 10, or a composition containing such.

31. A method for the treatment of disorders of coagulation comprising the administration to a subject of a pharmaceutically acceptable amount of a polymer according to any one of paragraphs 1 to 10, or a composition containing such.

32. A method for the treatment of inflammatory disorders comprising the administration to a subject of a pharmaceutically acceptable amount of a polymer according to any one of paragraphs 1 to 10, or a composition containing such.

33. The use of a polymer according to any one of paragraphs 1 to 10 in the preparation of a medicament for the treatment of cancer.

34. The use of a polymer according to any one of paragraphs 1 to 10 in the preparation of a medicament for the treatment of disorders of coagulation.

35. The use of a polymer according to any one of paragraphs 1 to 10 in the preparation of a medicament for the treatment of inflammatory disorders or conditions.

36. Polymers substantially as hereinbefore described with reference to Examples 6 or 7.

37. A method for the synthesis of polymers substantially as hereinbefore described with reference to Examples 6 or 7.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An antimicrobial copolymer for administration to humans or animals comprising polyethylene glycol and acrolein based monomer residues derived from base-catalyzed copolymerization in an aqueous solution of:
   (a) polyethylene glycol (PEG) of molecular weight selected from the range of from 200 to 2000 Daltons; and
   (b) acrolein based monomer selected from the group consisting of acrolein and/or its acetal derived with an hydroxyl-carboxylic acid;
wherein:
   the monomer ratio of PEG:acrolein based monomer residues within the copolymer is in the range of from 1:1 to 1:11;
   the copolymer remains soluble in aqueous solution; and
   the antimicrobial activity of the copolymer is not from release of acrolein based monomer into aqueous solution.

2. The antimicrobial copolymer according to claim 1 wherein the copolymer is soluble in water at less than pH 4.

3. The antimicrobial copolymer according to claim 1 wherein the copolymer is free of cross-linking or molecular conjugation.

4. The antimicrobial copolymer according to claim 1 comprising structures resulting from reaction between polyethylene glycol and proximate carbons to the carbonyl in acrolein based monomer residues formed during polymerization.

5. The antimicrobial copolymer according to claim 1 wherein the acrolein based monomer comprises acrolein acetal derived with a hydroxyl-alkanoic acid wherein the hydroxyl-alkanoic acid is selected from the group consisting of tartaric acid, lactic acid, glyceric acid, glycolic acid, citric acid and 2-hydroxy-butanoic acid.

* * * * *